(12) United States Patent
Berg-Schultz et al.

(10) Patent No.: US 7,906,108 B2
(45) Date of Patent: Mar. 15, 2011

(54) POLYSILOXANE SUNSCREENS

(75) Inventors: Katja Berg-Schultz, Muttenz/BL (CH);
Alexander Poschalko, Birsfelden (CH);
Jürgen H. Vollhardt, Ramlinsburg (CH)

(73) Assignee: DSM IP Assets B.V., Heerlen (NL)

( * ) Notice: Subject to any disclaimer, the term of this patent is extended or adjusted under 35 U.S.C. 154(b) by 617 days.

(21) Appl. No.: 11/920,430

(22) PCT Filed: May 23, 2006

(86) PCT No.: PCT/EP2006/004879
§ 371 (c)(1),
(2), (4) Date: Nov. 15, 2007

(87) PCT Pub. No.: WO2006/128614
PCT Pub. Date: Dec. 7, 2006

(65) Prior Publication Data
US 2009/0068127 A1    Mar. 12, 2009

(30) Foreign Application Priority Data

May 31, 2005 (EP) ..................... 05011678

(51) Int. Cl.
*C08G 77/26* (2006.01)
(52) U.S. Cl. .................. 424/59; 424/70.12; 424/70.122; 528/15; 528/31; 528/28; 528/26
(58) Field of Classification Search ................. 528/15, 528/31, 28; 424/59, 70.12, 70.122
See application file for complete search history.

(56) References Cited

U.S. PATENT DOCUMENTS

| | | | | |
|---|---|---|---|---|
| 5,061,479 A | * | 10/1991 | Grollier et al. | 424/47 |
| 5,223,249 A | * | 6/1993 | Forestier et al. | 424/59 |
| 6,004,540 A | * | 12/1999 | Richard et al. | 424/59 |

FOREIGN PATENT DOCUMENTS

| | | |
|---|---|---|
| EP | 0 570 577 | 11/1993 |
| EP | 0 709 080 A1 | 5/1996 |
| EP | 1 000 950 A2 | 5/2000 |
| EP | 1 081 140 A2 | 3/2001 |
| WO | 2004/007592 * | 1/2004 |
| WO | WO 2004/007592 A1 | 1/2004 |

OTHER PUBLICATIONS

International Search Report mailed Aug. 22, 2006 in PCT/EP2006/004879.
Written Opinion mailed Aug. 22, 2006 in PCT/EP2006/004879.

* cited by examiner

*Primary Examiner* — Margaret G Moore
(74) *Attorney, Agent, or Firm* — Nixon & Vanderhye P.C.

(57) ABSTRACT

The present invention relates to novel sunscreens on the basis of polysiloxanes, to their preparation and to their use, especially in formulations for the protection against harmful effects of sunlight.

15 Claims, No Drawings

POLYSILOXANE SUNSCREENS

This application is the U.S. national phase of international application PCT/EP2006/004879 filed 23 May 2006 which designated the U.S. and claims benefit of EP 05011678.9, dated 31 May 2005, the entire content of which is hereby incorporated by reference.

The present invention relates to novel sunscreens on the basis of polysiloxanes, to their preparation and to their use, especially in formulations for the protection against harmful effects of sunlight.

There is a constantly increasing need for sunscreen protection agents in a population that is exposed to an increasing amount of damaging sunlight. Repetitive sun exposure can result in skin changes known as photoaged skin. The clinical changes that are seen in photoaged skin differ from those of normally aged skin in sunlight protected sites of the body. Among the damaging results of intensive sun exposure of the skin there is increased wrinkling, elastosis, pigmentary changes, precancerous and cancerous skin lesions.

Many sunscreening chemicals have been developed in the past protecting against the harmful effects of UVA (320-400 nm) and/or UVB (290-320 nm) wavelengths. Very recently a new class of sun screening chemicals, the broadband UV-filters have been developed which shield the skin from UV-A and UV-B radiation. These chemicals have been incorporated either alone or in combination with each other into cosmetic or pharmaceutical preparations which are widely known and used. However, these is a need for the development of even more potent sunscreening chemicals and preparations containing them as well as of easier and economically more attractive chemical syntheses thereof, especially in view of further depletion of the ozon layer of the earth to be expected with concurrent increasing doses of UVA and UVB and even shorter wavelengths (UVC) to be endured.

The present invention, therefore, provides new polysiloxane-based sunscreen compounds, a method for their preparation and cosmetic or pharmaceutical compositions containing them.

More particularly the new compounds of the present invention are substituted polysiloxanes containing a certain number of the following structural elements per molecule, viz.

one element of formula $(H_3C)_3$—Si— (I), one element of formula —O—Si$(CH_3)_3$ (II), at least two elements selected from the groups (A), (B), (C) and (D)

(A) 0 to 100, preferably 5 to 60, elements in arbitrary order which are either identical or different from each other selected from the group consisting of formulae —O—Si$(CH_3)$[CH$(CH_3)$R$^1$]— (IIIa), —O—Si$(CH_3)$(CH$_2$—CH$_2$—R$^1$)— (IIIb), —O—Si$(CH_3)$[C(=CH$_2$)R$^1$]— (IIIc), and —O—Si$(CH_3)$(CH=CH—R$^1$)— (IIId);

(B) 0 to 100, preferably 5 to 60, elements in arbitrary order which are either identical or different from each other selected from the group consisting of formulae —O—Si$(CH_3)$[CH$(CH_3)$R$^2$]— (IVa), —O—Si$(CH_3)$(CH$_2$—CH$_2$—R$^2$)— (IVb), —O—Si$(CH_3)$[C(=CH$_2$)R$^2$]— (IVc), and —O—Si$(CH_3)$(CH=CH—R$^2$)— (IVd);

(C) 0 to 100, preferably 5 to 60, elements in arbitrary order which are either identical or different from each other selected from the group consisting of formulae —O—Si$(CH_3)$[CH$(CH_3)$R$^3$]— (Va), —O—Si$(CH_3)$(CH$_2$—CH$_2$—R$^3$)— (Vb), —O—Si$(CH_3)$[C(=CH$_2$)R$^3$]— (Vc), and —O—Si$(CH_3)$(CH=CH—R$^3$)— (Vd);

(D) 0 to 100, preferably 5 to 60, elements in arbitrary order which are either identical or different from each other selected from the group consisting of formulae —O—Si$(CH_3)$[CH$(CH_3)$R$^4$]— (VIa), —O—Si$(CH_3)$(CH$_2$—CH$_2$—R$^4$)— (VIb), —O—Si$(CH_3)$[C(=CH$_2$)R$^4$]— (VIc), and —O—Si$(CH_3)$(CH=CH—R$^4$)— (VId);

1-200, preferably 5 to 80 elements in arbitrary order of formula —O—Si$(CH_3)_2$— (VII) and optionally 1-20 elements in arbitrary order of formula —O—SiH$(CH_3)$— (VIII) are present,
wherein
R$^1$ is a UV-B light absorbing group,
R$^2$ is a UV-A light absorbing group,
R$^3$ is a UV-C light absorbing group and
R$^4$ is a broadband light absorbing group;
with the proviso that at least two elements belonging to different groups (A), (B), (C) and (D) are present.

The term "in arbitrary order" means that there is no specific order or sequence of the elements of formulae IIIa-IIId, IVa-IVd, Va-Vd, VIa-VId, VII and VIII in the polysiloxane molecule and that the order or sequence of the elements may vary from molecule to molecule.

Elements may be "identical" or "different from each other". This means that there may be present only one type of an element of formula IIIa-IIId and/or of formula IVa-IVd and/or of formula Va-Vd and/or of formula VIa-VId; or several elements of formula IIIa-IIId to formula VIa-VId. Thus, all possible combinations of different elements as defined above are comprised by the present invention. The sunscreen molecules of the present invention contain at least two different UV absorbing groups (chromophores), preferably, one type of UVA defined by formula IVa-IVd and one type of UVB absorbing groups defined by formula IIIa-IIId are present in the same molecule in arbitrary order to give protection against a broad wavelength spectrum. Additional groups with different absorption maxima, including UVC absorbing groups, may be present.

Thus, e.g., a polysiloxane compound of formula $(H_3C)_3$Si—[—O—Si$(CH_3)$(CH$_2$—CH$_2$—R$^1$)]$_7$—[—O—Si$(CH_3)_2$]$_{31}$—[—O—Si$(CH_3)$(CH$_2$—CH$_2$—R$^2$)]$_6$O—Si$(CH_3)_3$ contains in arbitrary order 44 silyloxy groups, 7 of which being groups of formula IIIb with chromophores R$^1$, 6 of which being groups of formula IVb with chromophores R$^2$, 31 of which being groups of formula IV.

The polysiloxane compounds of the present invention can be prepared by reacting a polydimethylhydrosiloxane of the general formula

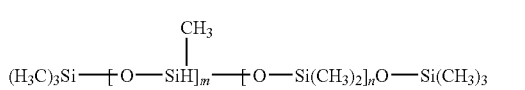

$$(IX)$$

wherein n+m is an integer of 4 to 520, preferably of 10 to 200 and more preferably of 20 to 60 and the ratio of n to m is 1:1 to 20:1, preferably 5:1 to 15:1.

with at least two terminally unsaturated compounds of the formulae

 (X)

 (XI)

wherein $R^{1-4}$ denotes one of the groups $R^1$, $R^2$, $R^3$ and $R^4$ are as defined above, with the proviso that the reactants X and XI comprise at least two different groups $R^{1-4}$, in the presence of a noble metal catalyst.

UV-light absorbing groups comprise all groups which absorb light in the range of wavelengths 400-320 nm (UVA) and 320-290 (UVB) or of even shorter wavelengths (UVC) and which are or can be used as chemical UV filters. The term "broadband light absorbing group" as used herein refers to groups which absorb light in a region overlapping UV-A and UV-B, especially in the range between about 310 and 360 nm. UV-light absorbing groups which may be present in compounds of the instant invention are, e.g., present in compounds belonging to the groups of acrylates, p-aminobenzoates, camphor derivatives (such as of benzylidene camphor type), cinnamates, benzophenones, esters of benzalmalonic acid, esters of 2-(4-ethoxy anilinomethylene)propandioic acid, imidazole derivatives, salicylates, triazone derivatives, triazol derivatives, dibenzoylmethanes, anthranilates, amino substituted hydroxybenzophenones, phenyl-benzimidazoles, phenyl-benzoxazoles, and 1,4-dihydropyranes.

Accordingly, the compounds of the formulas X and XI above comprise vinyl and ethynyl derivatives of such UV light absorbing compounds, especially those recited above, wherein the vinyl or ethynyl groups may be present, e.g., as a carboxyl ester group, or as an ether group, or as a vinyl or ethynyl substituted amino group.

Examples for acrylates include 2-ethylhexyl 2-cyano-3,3-diphenylacrylate (octocrylene, PARSOL® 340) and ethyl 2-cyano-3,3-diphenylacrylate;

Examples for p-aminobenzoates include 4-amino benzoic acid, 4-aminobenzoic acid-2,3-dihydroxypropylester, 4-(bis (2-hydroxypropyl)amino)benzoic acid ethyl ester, 4-(dimethylamino)benzoic acid-2-ethylhexylester (e.g. Eusolex® 6007) and ethoxylated 4-aminobenzoic acid ethyl ester (e.g. Uvinul® P25).

Examples for camphor derivatives include 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor and therephthalidene dicamphor sulfonic acid;

Examples for cinnamates include octyl methoxycinnamate (PARSOL® MCX), ethoxyethyl methoxycinnamate, diethanolamine methoxycinnamate (PARSOL® Hydro) and isoamyl methoxycinnamate.

Examples for benzophenones include benzophenone-3, benzophenone-4,2,2',4,4' tetrahydroxy-benzophenone and 2,2'Dihydroxy-4,4'dimethoxybenzophenone;

Examples for esters of benzalmalonic acid include di(2-ethylhexyl)4-methoxybenzalmalonate Examples for esters of 2-(4-ethoxy anilinomethylene)propandioic acid include 2-(4-ethoxy anilinomethylene)propandioic acid diethyl ester as described in the European Patent Publication EP 0895 776

Examples for imidazole derivatives include 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts and diethanolamine salts.

Examples for salicylate derivatives include isopropylbenzyl salicylate, benzyl salicylate, butyl salicylate, octyl salicylate (NEO HELIOPAN OS), isooctyl salicylate or homomethyl salicylate (homosalate, HELIOPAN);

Examples for triazone derivatives include octyl triazone (UVINUL T-150), dioctyl butamido triazone (UVASORB HEB).

Examples for triazol derivatives include benzotriazoles such as 2-(2-hydroxy-5-methylphanyl)benzotriazol, 2,2'-methylene-bis-(6-(2H-benzotriazole-2-yl)-4-(1,1,3,3-tetramethylbutyl)-phenol (TINOSORB M) as well as triazols described in EP-A-893119

Examples for dibenzoylmethane derivatives include compounds such as 4-tert. butyl-4'-methoxydibenzoyl-methane (PARSOL® 1789), dimethoxydibenzoylmethane and isopropyldibenzoylmethane;

Examples for Amino substituted hydroxybenzophenones include compounds such as 2-(4-Diethylamino-2-hydroxybenzoyl)-benzoic acid hexyl ester ester as described in the European Patent Publication EP 1046391

The UV-light absorbing groups or compounds mentioned above can be modified using methods well-known to a person skilled in the art, e.g. as described in more detail in the Examples or in analogy thereto, to yield compounds of formulae X and XI above.

Examples of preferred reactants of formulae X and XI are those comprising a benzalmalonate, a benzoxazol, a 1,4-dihydropyridine, a benzylidene champhor, a benzimidazol, a dibenzoylmethane, a p-amino benzoic acid, a benzotriazol or a hydroxybenzophenone group, illustrative examples being shown below:

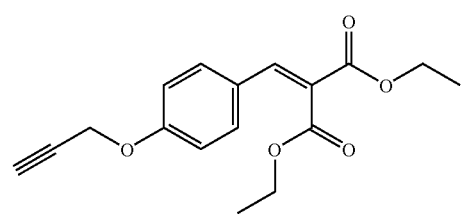

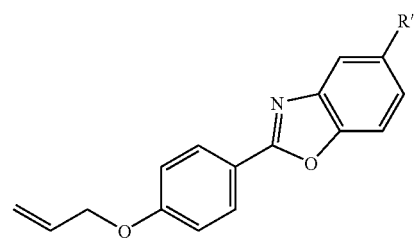

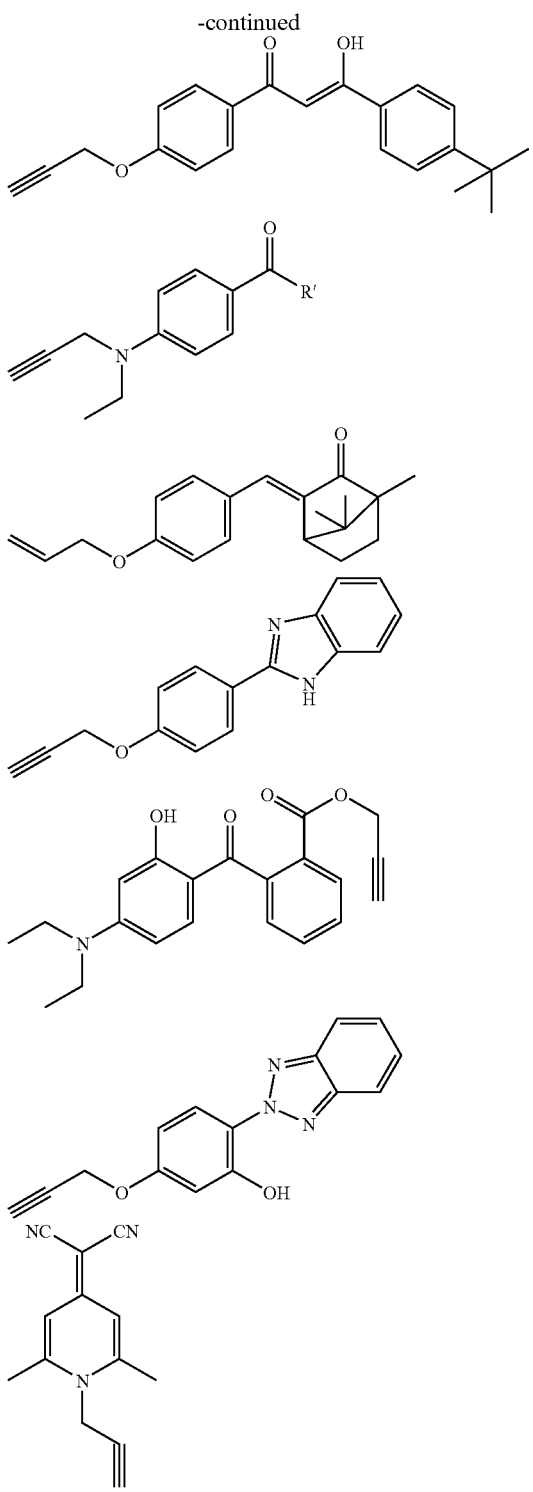

wherein R' is hydrogen, hydroxy, straight or branched chain $C_{1-20}$-alkyl, -alkoxy or $C_{2-20}$-alkenyl.

Examples of preferred polysiloxanes of the present invention are those wherein $R^1$ is derived from a benzalmalonate and $R^2$ is derived from an amino substituted hydroxybenzophenone, especially those obtained from reactants of the above structures.

The reaction of the polymethylhydrosiloxane of formula IX with the compounds of formulae X and/or XI to yield the compounds of the present invention can be carried out in a manner known per se, see, e.g., as described in WO 03/086340.

The reaction is suitably conducted in an organic solvent, e.g., an aliphatic, possibly chlorinated, or aromatic hydrocarbon such as toluene or xylene; an alcohol such as isopropanol; an ether such as THF; or a polar aprotic solvent, such as DMF, which is preferably part of the solvent as a solubilizer.

The reaction temperature, depending upon the reactants, is in the range of 40 to 150° C., preferably from 60° C. to 100° C., e.g., at about 80° C. The reaction time may vary between 2 and 48 hours.

Preferred noble metal catalysts are platinum metal catalysts, viz. Pt, Pd, Rh and Ru, with platinum being especially preferred. The catalyst can be in heterogeneous phase, e.g., on charcoal or, preferably, in homogeneous phase (Karstedt catalyst).

The reactants are reacted in the desired molecular ratios of the substituents $R^1$, $R^2$, $R^3$, and $R^4$ in the end product either simultaneously or successively under an inert gas atmosphere, preferably under nitrogen or argon. It is evident that the product obtained is a mixture of different polydimethylsiloxanes statistically substituted with residues carrying at least two UV-light absorbing groups chosen from $R^1$, $R^2$, $R^3$ and $R^4$.

Since the compounds of formulae X to XI can react in 1- or 2-position (of the terminal double or triple bond) with the polydimethylhydrosilane of formula IX a mixture of vicinal (1.2-substitution) and geminal (2.2-substitution)—relative to the terminal double or triple bond of compound X to XI—reaction products is obtained which can be used as sunscreens without previous separation of its components.

The ratio of UV-light absorbing groups of formula IIIa-d to VIa-d in the compounds of the present invention is not critical. Preferably a UV-B ($R^1$) and a UV-A ($R^2$) absorbing group in a ratio of 5:1 to 1:5, preferably 3:1 or 1:1, most preferred 2:1.

The ratio of the sum of the UV-light absorbing groups of formula IIIa-d to VIa-d to elements of formula VII is 1:20 to 1:1, preferably 1:15 to 1:5.

The so-obtained reaction product which comprises the compounds of the present invention may contain 1 to 20 elements of formula VIII, viz. unreacted elements from the starting material. This may be the case when sufficient amounts of reactants of formulae X and XI were lacking in the reaction mixture or did not react quantitatively for whatever reason. Such compounds may be eliminated, e.g., by a further reaction with a compound of the formula X or XI. Preferably, elements of formula VIII are absent or substantially absent from the compounds of the present invention.

The starting polydimethylhydrosiloxane material of formula are well known in the silicone industry and are commercially available (e.g. Wacker, GE-Bayer Silicones or Dow Corning) or can easily be prepared by a person skilled in the art from dichloro-methylsilane and trimethyl-chlorosilane, using the desired molecular ratios, in aqueous solution. They are described, for example, in the following patents: U.S. Pat. No. 3,220,972, U.S. Pat. No. 3,697,474 and U.S. Pat. No. 4,340,709.

The polysiloxane compounds of the present invention can be used as sunscreens. They are suitable for the protection of human skin and/or hair from damaging effects of UV radiation, as well as for protection of UV sensitive plastic materials, medicinal products and other objects.

Therefore, the polysiloxane compounds can be converted into compositions, particularly into topical compositions, in combination with pharmaceutically and/or cosmetically acceptable excipients.

The compositions comprising the compounds of the present invention are particularly suitable for topical applications onto human skin and/or hair.

If desired, additional UV-A and UV-B screening agents may be added to the cosmetic and/or dermatological compositions of the present invention. The combination of different UV filters may also show synergistic effects.

While the compounds of the present invention can be used alone or in combination with other compounds which absorb in the UV range, although at least an effective amount of a compound of the present invention should be present in the sunscreen compositions. The term "effective amount of the compound of the present invention" means generally at least 0.2% by weight based on the total weight of the sunscreen composition.

The total amount of UV screening agents, i.e. of the present compounds and, if desired, of additional UV-A/B screening agents, is not narrowly critical. Such amounts may vary from 0.2% by weight and higher, suitably between about 0.5 and about 20%, preferably between about 0.5 and about 12% by weight of the total amount of the composition.

Suitable UV-B screening agents which may be contained in the compositions of the present invention are, e.g., the following organic and inorganic compounds:

Acrylates, such as 2-ethylhexyl-2-cyano-3,3-diphenylacrylate (octocrylene, PARSOL® 340), ethyl 2-cyano-3,3-diphenylacrylate and the like;

camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like, as well as cinnamic acid derivatives bound to siloxanes;

p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate;

benzophenones, such as benzophenone-3, benzophenone-4,2,2', 4,4'-tetrahydroxy-benzophenone, 2,2'-dihydroxy-4,4'-dimethoxybenzophenone and the like;

esters of benzalmalonic acid such as di-(2-ethylhexyl)-4-methoxybenzalmalonate;

esters of 2-(4-ethoxy-anilinomethylene)-propandioic acid, such as 2-(4-ethoxy-anilinomethylene)-propandioic acid diethyl ester (EP-A2-0895 776);

organosiloxane compounds containing benzmalonate groups as described in the European Patent Publications EP-B1-0358584, EP-B1-0538431 and EP-A1-0709080;

drometrizole trisiloxane (Mexoryl XL);

pigments such as microparticulated $TiO_2$, and the like, the term "microparticulated" referring to a particle size from about 5 nm to about 200 nm, particularly from about 15 nm to about 100 nm. The $TiO_2$ particles may also be coated by metal oxides such as aluminum or zirconium oxide, or by organic coatings such as polyols, methicone, aluminum stearate, alkyl silane and the like, well known in the art;

imidazole derivatives such as, 2-phenyl benzimidazole sulfonic acid and its salts (PARSOL®HS), e.g., alkali salts such as sodium or potassium salts, ammonium salts, morpholine salts, salts of primary, sec. and tert. amines like monoethanolamine salts, diethanolamine salts and the like;

salicylate derivatives such as isopropylbenzyl salicylate, benzyl salicylate, butyl salicylate, octyl salicylate (NEO HELIOPAN OS), isooctyl salicylate or homomethyl salicylate (homosalate, HELIOPAN) and the like;

triazone derivatives such as octyl triazone (UVINUL T-150), dioctyl butamido triazone (UVASORB HEB) and the like.

Suitable conventional UV-A screening agents which may be contained in the compositions of the present invention are the following organic and inorganic compounds:

Dibenzoylmethane derivatives such as 4-tert.-butyl-4'-methoxydibenzoyl-methane (PARSOL® 1789), dimethoxydibenzoylmethane, isopropyldibenzoylmethane and the like;

benzotriazole derivatives such as 2,2'-methylene-bis-[6-(2H-benzotriazole-2-yl)-4-(1,1,3,3-tetramethylbutyl)-phenol] (TINOSORB M) and the like;

phenylene-1,4-bis-benzimidazolsulfonic acids or their salts such as 2,2-(1,4-phenylene)-bis-(1H-benzimidazol-4,6-disulfonic acid) (Neoheliopan AP);

amino substituted hydroxybenzophenones such as 2-(4-diethylamino-2-hydroxy-benzoyl)-benzoic acid hexylester as described in European patent publication EP 1046391;

pigments such as microparticulated ZnO and the like. The term "microparticulated" refers to a particle size from about 5 nm to about 200 nm, particularly from about 15 nm to about 100 nm. The ZnO particles may also be coated by metal oxides such as, e.g., aluminum or zirconium oxides or by organic coatings such as e.g. polyols, methicone, aluminum stearate, alkyl silane. Such coatings are well known in the art.

Because dibenzoylmethane derivatives are photolabile UV-A screening agents, it may be desirable to photostabilize them. Thus, the term "conventional UV-A screening agent" also refers to dibenzoylmethane derivatives such as e.g. PARSOL® 1789 stabilized by, e.g., 3,3-diphenylacrylate derivatives as described in EP-B1-0514491 and EP-A1-0780119;

benzylidene camphor derivatives as described in USP-5605680;

organosiloxanes containing benzmalonate groups as described in EP-B1-0358584, EP-B1-053843 and EP-A1-0709080.

The compositions of the invention can also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, in particular those suitable for providing an additional photoprotective effect by physically blocking out ultraviolet radiation, or any other ingredients usually formulated into cosmetics, in particular for the production of sunscreen/antisun compositions. The necessary amounts of the cosmetic and dermatological adjuvants and additives can, based on the desired product, easily be chosen by the skilled person.

Particularly preferred antioxidants are those chosen from the group consisting of amino acids (e.g. glycine, histidine, tyrosine, tryptophane) and their derivatives, imidazole (e.g. urocanic acid) and derivatives, peptides such as D,L-carnosine, D-carnosine, L-carnosine and derivatives (e.g. anserine), carotinoids, carotenes (e.g. β-carotene, γ-carotene, lycopene) and derivatives, chlorogenic acid and derivatives, liponic acid and derivatives (e.g. dihydroliponic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-, oleyl-, γ-linoleyl-, cholesteryl- and glycerylester) and the salts thereof, dilaurylthiodipropionate, distearylthiodipropionate, thiodipropionic acid and its derivatives (esters, ethers, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. from pmol to µmol/kg), additional (metal)-chelators (such as α-hydroxy fatty acids, palmic acid, phytinic acid, lactoferrin), α-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate, Mg-ascorbylphosphate, Na-ascorbylphosphate, ascorbylacetate), tocopherole and derivates (such as vitamin E acetate), vitamin A and derivatives (vitamin A palmitate) as well as coniferylbenzoat, rutinic acid and derivatives, α-glycosylrutin, ferulic acid, furfurylidenglucitol, carnosin, butylhydroxytoluene, butylhydroxyanisole, trihydroxybutyrophenone, urea and its derivatives; mannose and derivatives, zinc and derivatives (e.g. ZnO; ZnSO$_4$), Selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients.

The amount of the abovementioned preservatives and/or antioxidants (one or more compounds) in the preparations is preferably from 0.001 to 30% by weight, particularly preferably from 0.05 to 20% by weight, in particular from 1 to 10% by weight, based on the total weight of the preparation.

If vitamin E and/or derivatives thereof are used as the antioxidant(s), it is advantageous to choose their particular concentration from the range 0.001 to 10% by weight, based on the total weight of the formulation.

If vitamin A and/or derivatives thereof, or carotenoids are the antioxidant(s), it is advantageous to choose their particular concentration from the range 0.001 to 10% by weight, based on the total weight of the formulation.

The compositions according to the present invention may also contain emulsifiers. An emulsifier enables two or more immiscible liquids to be combined homogeneously, while increasing the viscosity of the composition. Moreover, the emulsifier acts to stabilize the composition.

Emulsifiers that may be used according to the present invention, to form O/W, W/O and/or O/W/O formulations, include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and salts thereof such as cetyl phosphate, DEA cetyl phosphate, potassium cetyl phosphate, sodium glyceryl oleate phosphate, hydrogenated vegetable glyceride phosphates and mixtures thereof. Furthermore, one or more synthetic polymers may be used as emulsifiers. For example, PVP eicosaene copolymer, acrylates/C10-C30 alkyl acrylate crosspolymer, acrylates/steareth methacrylate copolymer, PEG-22/dodecyl glycol copolymer, PEG-45/dodecyl glycol copolymer, and mixtures thereof. Preferred emulsifiers are PVP eicosaene copolymer, acrylates/C10-C30 alkyl acrylate crosspolymer, PEG-20 sorbitan isostearate, sorbitan isostearate, and mixtures thereof.

The emulsifier may be present in a total amount varying from about 0.01 wt. % to about 15 wt. %, preferably from about 0.1 wt. % to about 3 wt. %, of the total weight of the composition.

The fatty/oily phase is advantageously chosen from:
mineral oils and mineral waxes;
oils such as triglycerides of caprinic acid or caprylic acid, preferably castor oil;
natural or synthetic oils, preferably esters of carbonic acids or fatty acids with alcohols, e.g., such as isopropanol, propyleneglycol or glycerine;
alkylbenzoates and
silicone oils such as dimethylpolysiloxane, diethylpolysiloxane, diphenylpolysiloxane and mixtures thereof.

Fatty substances which can be incorporated into the oily phase of the compositions according to the invention are advantageously chosen from esters of saturated and/or unsaturated, straight or branched chain alkyl carboxylic acids with 3 to 30 carbon atoms, and saturated and/or unsaturated, straight and/or branched chain alcohols with 3 to 30 carbon atoms, as well as esters of aromatic carboxylic acids and of saturated and/or unsaturated, straight or branched chain alcohols of 3 to 30 carbon atoms. Such esters can advantageously be selected from octylpalmitate, octylcocoate, octylisostearate, octyldodecylmyristate, cetylisononanoate, isopropylmyristate, isopropylpalmitate, isopropylstearate, isopropyloleate, n-butylstearate, n-hexyllaurate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as from synthetic, halfsynthetic and natural mixtures of such esters such as jojoba oil.

Other fatty components suitable for use in the compositions according to the present invention include polar oils such as lecithines and fatty acid triglycerides, namely triglycerinic esters of saturated and/or unsaturated, straight or branched chain carbonic acids with 8 to 24 carbon atoms, preferably of 12 to 18 carbon atoms whereas the fatty acid triglycerides are preferably chosen from synthetic, half synthetic and natural oils (e.g. cocoglyceride, olive oil, sun flower oil, soybean oil, peanut oil, rape oil, almond oil, palm oil, coconut oil, castor oil, hydrogenated castor oil, wheat oil, grape oil and others); apolar oils such as linear and/or branched chain hydrocarbons and waxes, e.g., mineral oils, vaseline (petrolatum); paraffins, squalan and squalen, polyolefines (favored are polydecenes), hydrogenated polyisobutenes and isohexadecanes; dialkyl ethers such as dicaprylylether; linear or cyclic silicone oils such as cyclomethicone, octamethylcyclotetrasiloxane, cetyldimethicone, hexamethylcyclotrisiloxane, polydimethylsiloxane, poly-(methylphenylsiloxan) and mixtures thereof.

Other fatty components which can advantageously be incorporated into the compositions of the present invention are isoeikosane; neopentylglycoldiheptanoate; propylenglykoldicaprylate/-dicaprate; caprylic-/capric-/diglycerylsuccinate; butylenglykol caprylat/caprat; C12-13 alkyllactate; di-C12-13 alkyltartrate; triisostearin; dipentaerythrityl hexacaprylat/hexacaprate; propylenglykolmonoisostearate; tricaprylin; dimethylisosorbid. Particularly preferred is the use of mixtures of C12-15 alkylbenzoate and 2-ethylhexylisostearate, mixtures of C12-15 alkylbenzoate and isotridecylisononanoate as well as mixtures of C12-15 alkylbenzoate, 2-ethylhexylisostearate and isotridecylisononanoate.

The oily phase of the compositions according to the present invention can also contain natural vegetable or animal waxes such as bee wax, china wax, bumblebee wax and other waxes of insects as well as sheabutter.

The compositions according to the present invention may additionally contain one or more emollients. An emollient provides a softening or soothing effect on the skin surface and is generally considered safe for topical use. Emollients also help control the rate of evaporation and the tackiness of the composition. Preferred emollients include mineral oil, lanolin oil, coconut oil, cocoa butter, olive oil, aloe extracts, jojoba oil, castor oil, fatty acids such as oleic and stearic acid, fatty alcohols such as cetyl and hexadecyl alcohol diisopropyl adipate, benzoic and hydroxybenzoic acid esters of $C_9$-$C_{15}$ alcohols, isononyl iso-nonanoate, $C_{15}$-$C_{50}$ alkanes, mineral oil, silicones such as dimethyl polysiloxane, ethers such as polyoxypropylene butyl ethers and polyoxypropylene cetyl ethers, and $C_2$-$C_{15}$ alkyl benzoates, and mixtures thereof. The most preferred emollients are hydroxybenzoate esters, aloe vera, $C_{12-15}$ alkyl benzoates, and mixtures thereof.

The emollient is present in an amount varying from about 1 wt. % to about 20 wt. %, preferably from about 2 wt. % to about 15 wt. %, and most preferrably from about 4 wt. % to about 10 wt. % of the total weight of the composition.

The aqueous phase of the formulations of the present invention can contain the usual cosmetic additives such as alcohols, especially lower alcohols, preferably ethanol and/or isopropanol, low alkyl diols or polyols and their ethers, preferably propyleneglycol, glycerine, ethyleneglycol, ethyleneglycolmonoethyl- or -monobutyl ether, propyleneglycolmonomethyl-, -monoethyl- or -monobutyl ether, diethyleneglycolmonomethyl- or -monoethyl ether and analogue products, polymers, foam stabilisators; electrolytes and, especially, one or more thickeners.

Thickeners that may be used in formulations of the present invention include the family of siliciumdioxide, magnesium and/or aluminum silicates, polysaccharides and their derivatives such as hyaluronic acid, xanthan gum, hydroxypropyl cellulose, acrylate copolymers, preferably a polyacrylate of the family of carbopoles, such as carbopoles of type 980, 981, 1382, 2984, 5984.

Moisturizing agents, such as humectants, may be incorporated into the compositions according to the present invention to reduce the trans-epidermal water loss (TEWL) of the horny layer of the skin. Suitable humectants include glycerin, lactic acid, pyrrolidone carbonic acid, urea, polyethylene glycol, polypropylene glycol, sorbitol, PEG-4, and mixtures thereof. Additional suitable moisturizers are polymeric moisturizers of the family of water soluble and/or with water gelating polysaccharides such as hyaluronic acid, chitosan and/or fucose rich polysaccharides available, e.g., as Fucogel®1000 (CAS-Nr. 178463-23-5) from SOLABIA S. The moisturizing agent is optionally present in an amount varying from about 0.5 wt. % to about 8 wt. %, preferably from about 1 wt. % to about 5 wt. % of the total weight of the composition.

Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, trisodium ethylenediaminetetraacetic acid and mixtures thereof; basic amino acids such as arginine and lysine and any combination of any of the foregoing. The neutralizing agent may be present in an amount of about 0.01 wt. % to about 8 wt. % in the compositions of the present invention, preferably, 1 wt. % to about 5 wt. %.

The addition of electrolytes into the composition of the present invention may be necessary to change the behavior of a hydrophobic emulsifier. Thus the emulsions/microemulsions of this invention may preferably contain electrolytes of one or several salts including anions such as a chloride, a sulfate, a carbonate, a borate or an aluminate, without being limited thereto. Other suitable electrolytes may be on the bases of organic anions such as, but not limited to, lactate, acetate, benzoate, propionate, tartrate and citrate. As cations preferably ammonia, alkylammonia, alkali- or alkaline earth metals, magnesium-, iron- or zinc-ions are selected. Especially preferred salts are potassium and sodium chloride, magnesium sulfate, zinc sulfate and mixtures thereof. Electrolytes are present in an amount of about 0.01 wt. % to about 8 wt. % in the compositions of the present invention.

The cosmetic compositions of the invention are useful as compositions for photoprotecting the human epidermis or hair against the damaging effect of UV irradiation, as antisun/sunscreen composition or as makeup product. Such compositions can, in particular, be provided in the form of a lotion, a thickened lotion, a gel, a cream, a milk, an ointment, a powder or a solid tube stick and may optionally be packaged as an aerosol and may be provided in the form of a mousse, foam or a spray. When the cosmetic composition according to the invention is provided for protecting the human epidermis against UV radiation or as antisun/sunscreen composition, it may be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

When the cosmetic composition according to the invention is used for protecting the hair, it may be in the form of a shampoo, a lotion, a gel or a rinse out composition, to be applied before or after shampooing, before or after dyeing or bleaching, before, during or after permanent-waving or hair straightening operation, a styling or treatment lotion or a gel, a blow-drying or hairsetting lotion or gel, a hair lacquer, or a composition for permanent-waving, straightening, dyeing or bleaching the hair.

To protect human hair against UV rays, the compounds of the invention can be incorporated into shampoos, lotions, gels, hairsprays, aerosol foam creams or emulsions in concentrations of from 0.1 to 10% by weight, preferably from 1 to 7% by weight. The respective formulations can be used, inter alia, for washing, coloring and for styling the hair.

When the cosmetic composition according to the invention is used as makeup product for eyelashes, the eyebrows, the skin or the hair, such as an epidermal treatment cream, a foundation, a tube of lipstick, an eyeshadow, a face powder, an eyeliner, a mascara or a coloring gel, it may be solid or pasty, anhydrous or in aqueous form, such as O/W or W/O emulsion, suspension or gel.

The present invention also features formulating the polysiloxane compounds according to the invention as agents for screening out UV radiation, in particular for controlling the color of human skin.

The polysiloxane compounds according to this invention show an excellent liposolubility and can thus be incorporated in high concentrations into cosmetic formulations leading to a high protection factor of the final compositions. Additionally they are homogeneously distributed in the cosmetic formulation containing at least a fatty phase and a cosmetically accepted organic solvent which leads, applied on the skin/or hair, to the formation of a protective film which protects effectively the skin and/or hair against the deleterious effects of UV-radiation.

Thus, it is another object of the present invention to use the compounds and compositions of the invention for protecting the skin and/or hair against UV radiation, in particular solar radiation, comprising topically applying an effective amount of a cosmetic composition containing the polysiloxane compounds according to the invention.

Finally, according to another embodiment of the invention, a polysiloxane compound or compositions of this invention can be used as protecting agents against UV radiation for plastics and other UV sensitive materials and products.

The following examples are provided to further illustrate the processes and compositions of the present invention. These examples are illustrative only and are not intended to limit the scope of the invention in any way. In the Examples, FC. means Flash chromatography; HV means high vacuum (0.1 Pa or below); INCI means International Nomenclature Cosmetic Ingredients. The term "Polymeric broadband filter" refers to a polysiloxane as defined in claim 1, especially as prepared in Example 1 or 2. All structures were unambiguously identified via $^1$H-NMR (300 MHZ, CDCl$_3$). The photostability of the products were measured according to Berset et. al.; Internat. J. Cosmetic Science 18:167-177 (1996).

EXAMPLE 1

A: Preparation of 2-(4-diethylamino-2-hydroxybenzoyl)benzoic acid prop-2-ynyl ester A solution of 200 mmol 2-(4-diethylamino-2-hydroxybenzoyl)benzoic acid, 500 mmol propargylic alcohol, 220 mmol 1-(3-dimethylaminopropyl)-3-ethylcarbodiimide hydrochloride (EDC), and 500 mmol N-ethyldiisopropylamine in 600 mL DMF is stirred at room temperature for 2 h. 1 L of ethyl acetate is added and the solution extracted with 1 L water. The organic layer is separated, dried (Na$_2$SO$_4$), and the solvent evaporated. The crude product is purified via FC (n-hexane/EtOAC 2:1) yielding 2-(4-diethylamino-2-hydroxybenzoyl)benzoic acid prop-2-ynyl ester. MS (EI): 374 (18%, M+Na$^+$), 352 (100%, M+H$^+$), 296 (17%). UV (EtOH): $\lambda_{max}$=356 nm ($\epsilon$=31'648).

B: Preparation of Polysiloxane Copolymer Containing Groups of Formula III c wherein R$^1$ is 4-[(2,2-diethoxycarbonyl)-vinyl]-phenoxymethyl and of formula VIc wherein R$^2$ is 2-(4-diethylamino-2-hydroxybenzoyl)-benzoyloxymethyl and of Formula VII with a Statistical distribution as Depicted Below

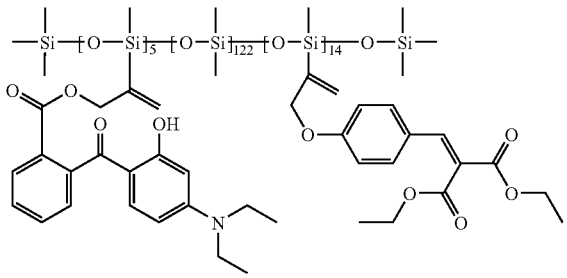

A solution of 2.55 mmol of 2-(4-diethylamino-2-hydroxybenzoyl)benzoic acid prop-2-ynyl ester, 6.45 mmol 2-(4-prop-2-ynyloxy-benzylidene)-malonic acid diethyl ester of 2-(4-prop-2-ynyloxy-benzylidene)-malonic acid diethyl ester (prepared according to G. Frater et. al., EP 05380 431 [1991], Example 1), and 9.0 mmol eq. SiH of an organosiloxane of formula IV wherein B, B', R$^1$ and R$^2$ are methyl, Z is H, r is in its statistical mean 122 and s is in its statistical mean 19 in 20 ml toluene under an inert atmosphere is heated to 80° C. A catalytic amount of platinum carbon 5% is added and the reaction is kept at 80° C. for 24 h. Active charcoal is added and the mixture is stirred for 1 h at RT. After filtration over Celite the solvent is evaporated and the crude product purified by preparative GPC (Bio-Beads® S-X3) to yield a yellow oil. UV-A (THF): 352 nm (E=105), UV-B (THF): 312 nm (E=256) having unlimited solubility in Cétiol LC and Crodamol DA and excellent photostability qualities in a conventional formulation.

EXAMPLE 2

Preparation of Polysiloxane Copolymer Containing Groups of Formula IIIc wherein R$^1$ is 4-[(2,2-diethoxycarbonyl)-vinyl]-phenoxymethyl and of Formula VIc wherein R$^2$ is 2-(4-diethylamino-2-hydroxybenzoyl)-benzoyloxymethyl and of Formula VII with a Statistical Distribution as Depicted Below

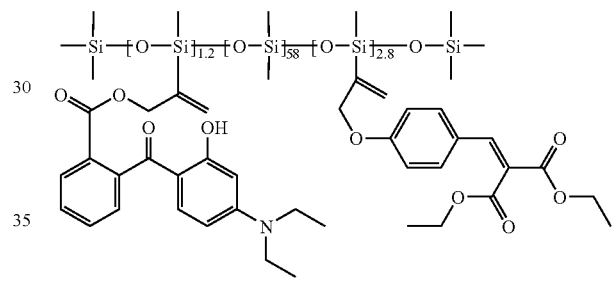

A solution of 1.2 mmol of 2-(4-diethylamino-2-hydroxybenzoyl)benzoic acid prop-2-ynyl ester, 2.95 mmol 2-(4-prop-2-ynyloxy-benzylidene)-malonic acid diethyl ester, and 5.0 g polysiloxane AE-151 of Wacker-Chemie GmbH (4.15 mmol eq. SiH) in 20 ml toluene under an inert atmosphere is heated to 80° C. A catalytic amount of platinum carbon 5% is added and the reaction is kept at 80° C. for 24 h. Active charcoal is added and the mixture is stirred for 1 h at RT. After filtration over Celite the solvent is evaporated and the crude product purified by preparative GPC (Bio-Beads® S-X3) to yield a yellow oil. UV-A (EtOH): 354 nm (E=50), UV-B (EtOH): 312 nm (E=129) having unlimited solubility in Cétiol LC and Crodamol DA and excellent photostability qualities in a conventional formulation.

EXAMPLE 3

| O/W sun milk | | |
|---|---|---|
| Ingredients | INCI Nomenclature | % w/w |
| A) PARSOL SLX | Dimethico Diethylbenzalmalonate-Polysilicone-15 | 6.00 |
| Neo Heliopan AP | | 3.00 |
| Tinosorb S | Hydrogenated Cocoglycerides | 3.00 |
| Lanette O | Cetearyl Alcohol | 2.00 |

-continued

O/W sun milk

| Ingredients | INCI Nomenclature | % w/w |
|---|---|---|
| Myritol 318 | Caprylic/capric Triglyceride | 6.00 |
| Mineral oil | Mineral oil | 2.00 |
| Vitamin E acetate | Tocopheryl Acetate | 1.00 |
| Prisorine 3515 | Isostearyl Alcohol | 4.00 |
| B) Edeta BD | Disodium EDTA | 0.10 |
| Phenonip | Phenoxyethanol & Methylparaben & Ethylparaben & Propylparaben & Butylparaben | 0.60 |
| Amphisol K | Potassium Cetyl Phosphate | 2.00 |
| Water deionized | Aqua | ad 100 |
| 1,2-Propylene Glycol | Propylene Glycol | 5.00 |
| Carbopol 981 | Carbomer | 0.30 |
| Tinosorb M | Methylene Bis-Benzotriazolyl Tetramethylbutylphenol | 6.00 |
| KOH 10% solution | Potassium Hydroxyde | 2.10 |
| C) 'Polymeric broadbandfilter' | | 1-20 |

Procedure:

Heat part A) and B) to 85° C. while stirring. When homogeneous, add part B) to A) under agitation. Cool to ambient temperature while stirring and add part C). Homogenize to achieve a small particle size.

EXAMPLE 4

Sun milk waterproofed

| | Ingredients | INCI Nomenclature | % w/w |
|---|---|---|---|
| A) | PARSOL SLX | Polysilicone-15Dimethico Diethylbenzalmalonate | 6.00 |
| | PARSOL 1789 | Butyl Methoxydibenzoylmethane | 2.00 |
| | PARSOL 5000 | 4-Methylbenzylidene Camphor | 4.00 |
| | Uvinul T 150 | Ethylhexyltriazone | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 0.60 |
| | Amphisol | Cetyl Phosphate DEA | 2.00 |
| B) | Water deionized | Aqua | ad 100 |
| | Propylene Glycol | Propylene Glycol | 5.00 |
| | Carbopol 980 | Carbomer | 0.30 |
| | KOH (10% sol.) | Potassium Hydroxide | 1.50 |
| C) | 'Polymeric broadbandfilter' | | 1-20 |

Procedure:

Heat part A) and B) to 85° C. while stirring. When homogeneous, add part B) to A) under agitation. Cool to ambient temperature while stirring and add part C). Homogenize to achieve a small particle size.

EXAMPLE 5

Sun milk for babies and children

| | Ingredients | INCI Nomenclature | % w/w |
|---|---|---|---|
| A) | Tegosoft TN | C12-15 Alkyl Benzoate | 5.00 |
| | Silicone 2503 Cosmetic Wax | Stearyl Dimethicone | 2.00 |
| | Cetyl Alcohol | Cetyl Alcohol | 1.00 |
| | Butylated Hydroxytoluene | BHT | 0.05 |
| | Estol GMM 3650 | Glyceryl Myristate | 4.00 |
| | Edeta BD | Disodium EDTA | 0.10 |
| | Phenonip | Phenoxyethanol & Methylparaben & Ethylparaben & Propylparaben & Butylparaben | 0.60 |
| | Amphisol A | Cetyl Phosphate | 2.00 |
| B) | Water deionized | Aqua | ad 100 |
| | Carbopol 980 | Carbomer | 0.6 |
| | Glycerine | Glycerine | 3.00 |
| | KOH sol. 10% | Potassium Hydroxide | 2.4 |
| C) | 'Polymeric broadbandfilter' | | 1-20 |

Procedure:

Heat part A) and B) to 85° C. while stirring. When homogeneous, add part B) to A) under agitation. Cool to ambient temperature while stirring and add part C). Homogenize to achieve a small particle size.

EXAMPLE 6

High protective sun milk

| | Ingredients | INCI Nomenclature | % w/w |
|---|---|---|---|
| A) | PARSOL SLX | Polysilicone-15Dimethico Diethylbenzalmalonate | 6.00 |
| | PARSOL 1789 | Butyl Methoxydibenzoylmethane | 2.00 |
| | PARSOL 5000 | 4-Methylbenzylidene Camphor | 4.00 |
| | Uvinul T 150 | | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 0.60 |
| | Amphisol K | Potassium Cetyl Phosphate | 2.00 |
| B) | Water deionized | Aqua | ad 100 |
| | Propylene Glycol | Propylene Glycol | 5.00 |
| | Carbopol 980 | Carbomer | 0.30 |
| | KOH (10% sol.) | Potassium Hydroxide | 1.50 |
| C) | 'Polymeric broadbandfilter' | | 1-20 |
| D) | Perfume | Perfume | q.s. |

Procedure:

Heat part A) and B) to 85° C. while stirring. When homogeneous, add part B) to A) under agitation. Cool to ambient temperature while stirring and add part C) and D). Homogenize to achieve a small particle size.

EXAMPLE 7

Water-free sun gel

| | Ingredients | INCI Nomenclature | % w/w |
|---|---|---|---|
| A) | PARSOL MCX | Ethylhexyl Methoxycinnamate | 6.00 |
| | PARSOL 1789 | Butyl Methoxydibenzoylmethane | 4.00 |
| | PARSOL 5000 | 4-Methylbenzylidene Camphor | 4.00 |
| | Uvasorb HEB | Diethylhexyl Butamido Triazone | 1.50 |
| | Uvinul A plus | | 2.00 |
| | Vitamin E acetate | Tocopheryl Acetate | 1.50 |
| | Tegosoft TN | C12-15 Alkyl Benzoate | 9.00 |
| | Elefac I-205 | Ethylhexyldodecyl Neopentanoate | 2.00 |
| | Alcohol | Alcohol | ad 100 |
| | Isopropyl Alcohol | Isopropyl Alcohol | 20.00 |
| B) | Klucel MF | Hydroxypropylcellulose | 2.00 |
| C) | 'Polymeric broadbandfilter' | | 1-20 |
| D) | perfume | | q.s. |

Procedure:

Mix part A) and B) while stirring. When homogeneous, add part C) and D) under agitation.

EXAMPLE 8

Sun gel

| | Ingredients | INCI Nomenclature | % w/w |
|---|---|---|---|
| A) | Pemulen TR-2 | Acrylates/C10-30 Alky Acrylate Crosspolymer | 0.60 |
| | Phenonip | Phenoxyethanol & Methylparaben & Ethylparaben & Propylparaben & Butylparaben | 0.60 |
| | Edeta BD | Disodium EDTA | 0.1 |
| | Aqua | Aqua | ad 100 |
| B) | PARSOL 1789 | Butyl Methoxydibenzoylmethane | 4.00 |
| | PARSOL 340 | Octocrylene | 3.00 |
| | Tegosoft TN | C12-15 Alkyl Benzoate | 15.00 |
| | Antaron V-216 | PVP/Hexadecene Copolymer | 1.00 |
| | Vitamin E acetate | Tocopheryl Acetate | 0.50 |
| | Butylated Hydroxytoluene | BHT | 0.05 |
| | Cremophor RH 410 | PEG-40 Hydrogenated Castor Oil | 0.50 |
| | Tris Amino | Tromethamine | 0.50 |
| C) | 'Polymeric broadbandfilter' | | 1-20 |
| D) | Perfume | Perfume | q.s. |

Procedure:

Heat part A) and B) to 85° C. while stirring. When homogeneous, add part B) to A) under agitation. Cool to ambient temperature while stirring and add part C) and D). Homogenize to achieve a small particle size.

EXAMPLE 9

High protection WO sun milk

| | Ingredients | INCI Nomenclature | % w/w |
|---|---|---|---|
| A) | PARSOL 1789 | Butyl Methoxydibenzoylmethane | 2.00 |
| | PARSOL 5000 | 4-Methylbenzylidene Camphor | 4.00 |
| | Uvinul T 150 | Ethylhexyl Triazone | 2.00 |

High protection WO sun milk (continued)

| | Ingredients | INCI Nomenclature | % w/w |
|---|---|---|---|
| | Uvinul TiO2 | Titanium Dioxide and Trimethoxycaprylylsilane | 5.00 |
| | Arlacel P 135 | PEG-30 Dipolyhydroxystearate | 2.00 |
| | Tegosoft TN | C12-15 Alkyl Benzoate | 5.00 |
| | Cosmacol EMI | Di-C12-13 Alkyl Malate | 6.00 |
| | Miglyol 840 | Propylene Glycol Dicaprylate/Dicaprate | 6.00 |
| | Butylated Hydroxytoluene | BHT | 0.05 |
| | Phenonip | Phenoxyethanol & Methylparaben & Ethylparaben & Propylparaben & Butylparaben | 0.60 |
| B) | Deionized water | Aqua | ad 100 |
| | Glycerin | Glycerin | 5.00 |
| | Edeta | Disodium EDTA | 0.1 |
| | NaCl | Sodium Chloride | 0.30 |
| C) | PARSOL HS | Phenylbenzyimidazole Sulphonic Acid | 4.00 |
| | Water | Aqua | 20.00 |
| | Triethanolamine 99%. | Triethanolamine | 2.50 |
| D) | 'Polymeric broadbandfilter' | | 1-20 |
| E) | Perfume | | q.s. |

Procedure:

Heat part A), B) and C) to 85° C. while stirring. When homogeneous, add part B) and C) to A) under agitation. Cool to ambient temperature while stirring and add part D) and E). Homogenize to achieve a small particle size.

EXAMPLE 10

W/O milk with pigments

| | Ingredients | INCI Nomenclature | % w/w |
|---|---|---|---|
| A) | Cremophor WO 7 | PEG-7 Hydrogenated Castor Oil | 6.00 |
| | Elfacos ST 9 | PEG-45/Dodecyl Glycol Copolymer | 2.00 |
| | PARSOL 1789 | Butyl Methoxydibenzoylmethane | 3.00 |
| | Tinosorb S | | 5.00 |
| | PARSOL 5000 | 4-Methylbenzylidene Camphor | 4.00 |
| | microfine ZnO | Zinc Oxide | 2.00 |
| | Microcrystalline wax | Microcrystalline Wax | 2.00 |
| | Miglyol 812 | Caprylic/capric Triglyceride | 5.00 |
| | Vitamin E acetate | Tocopheryl Acetate | 1.00 |
| | Jojoba oil | *Simmondsia Chinensis* Seed Oil | 5.00 |
| | Edeta BD | Disodium EDTA | 0.10 |
| | Butylated Hydroxytoluene | BHT | 0.05 |
| | Phenonip | Phenoxyethanol & Methylparaben & Ethylparaben & Propylparaben & Butylparaben | 0.60 |
| B) | Water deionized | Aqua | ad 100 |
| | Glycerin | Glycerin | 5.00 |
| C) | Neo Heliopan AP | | 2.00 |
| | Water deionized | Aqua | 20.00 |
| | KOH 10% solution | Potassium Hydroxide | 4.00 |
| D) | 'Polymeric broadbandfilter' | | 1-20 |
| E) | Perfume | Perfume | q.s. |

Procedure:

Heat part A), B) and C) to 85° C. while stirring. When homogeneous, add part B) and C) to A) under agitation. Cool to ambient temperature while stirring and add part D) and E). Homogenize to achieve a small particle size.

EXAMPLE 11

| | Protective Day cream with Vitamin C | | |
|---|---|---|---|
| | Ingredients | INCI Nomenclature | % w/w |
| A) | PARSOL SLX | Polysilicone-15 Dimethico Diethylbenzalmalonate | 4.00 |
| | PARSOL 1789 | Butyl Methoxydibenzoylmethane | 1.50 |
| | Glyceryl Myristate | Glyceryl Myristate | 2.00 |
| | Cetyl Alcohol | Cetyl Alcohol | 0.50 |
| | Myritol 318 | Caprylic/Capric Triglyceride | 5.00 |
| | Crodamol DA | Diisopropyl Adipate | 5.00 |
| | Vitamin E acetate | Tocopheryl Acetate | 2.00 |
| | Butylated Hydroxytoluene | BHT | 0.05 |
| | Phenonip | Phenoxyethanol & Methylparaben & Ethylparaben & Propylparaben & Butylparaben | 0.60 |
| | Edeta BD | Disodium EDTA | 0.10 |
| | Amphisol K | Potassium Cetyl Phosphate | 2.00 |
| B) | Water deionized | Aqua | ad 100 |
| | 1,2-Propylene Glycol | Propylene Glycol | 2.00 |
| | D-Panthenol 75 L | Panthenol | 2.00 |
| | Ethanol | Ethanol | 5.00 |
| | Allantoin | Allantoin | 0.20 |
| | Carbopol ETD 2001 | Carbomer | 0.30 |
| | KOH 10% sol. | Potassium Hydroxide | 1.50 |
| C) | Water | Aqua | 10.00 |
| | Stay-C 50 | Sodium Ascorbyl Phosphate | 0.50 |
| D) | 'Polymeric broadbandfilter' | | 1-20 |
| E) | Perfume | Perfume | q.s. |

What is claimed is:

1. Polysiloxanes comprising the following structural elements per molecule:

one element of formula $(H_3C)_3$—Si— (I), one element of formula —O—Si$(CH_3)_3$ (II), at least two elements selected from the groups (A), (B), (C) and (D), (A) 0 to 100 elements in arbitrary order which are either identical or different from each other selected from the group consisting of formulae —O—Si$(CH_3)$[CH$(CH_3)R^1$]— (IIIa), —O—Si$(CH_3)$(CH$_2$—CH$_2$—R$^1$)— (IIIb), —O—Si$(CH_3)$[C(=CH$_2$)R$^1$]— (IIIc), and —O—Si$(CH_3)$(CH=CH—R$^1$)— (IIId);

(B) 0 to 100 elements in arbitrary order which are either identical or different from each other selected from the group consisting of formulae —O—Si$(CH_3)$[CH$(CH_3)R^2$]— (IVa), —O—Si$(CH_3)$(CH$_2$—CH$_2$—R$^2$)— (IVb), —O—Si$(CH_3)$[C(=CH$_2$)R$^2$]— (IVc), and —O—Si$(CH_3)$(CH=CH—R$^2$)— (IVd);

(C) 0 to 100 elements in arbitrary order which are either identical or different from each other selected from the group consisting of formulae —O—Si$(CH_3)$[CH$(CH_3)R^3$]— (Va), —O—Si$(CH_3)$(CH$_2$—CH$_2$—R$^3$)— (Vb), —O—Si$(CH_3)$[C(=CH$_2$)R$^3$]— (Vc), and —O—Si$(CH_3)$(CH=CH—R$^3$)— (Vd);

(D) 0 to 100 elements in arbitrary order which are either identical or different from each other selected from the group consisting of formulae —O—Si$(CH_3)$[CH$(CH_3)R^4$]— (VIa), —O—Si$(CH_3)$(CH$_2$—CH$_2$—R$^4$)— (VIb), —O—Si$(CH_3)$[C(=CH$_2$)R$^4$]— (VIc), and —O—Si$(CH_3)$(CH=CH—R$^4$)— (VId);

1-200 elements in arbitrary order of formula —O—Si$(CH_3)_2$—(VII), and optionally 1-20 elements in arbitrary order of formula —O—SiH$(CH_3)$—(VIII), wherein $R^1$ is a UV-B light absorbing group,
$R^2$ is a UV-A light absorbing group,
$R^3$ is a UV-C light absorbing group, and
$R^4$ is a broadband light absorbing group;
with the proviso that the molecule comprises at least two elements belonging to different groups (A), (B), (C) and (D).

2. The polysiloxanes according to claim 1 wherein the number of elements of group (A) is 1 to 50 and the number of elements of group (B) is 1 to 50.

3. The polysiloxanes according to claim 1 containing 5 to 80 elements in arbitrary order of formula —O—Si$(CH_3)_2$—.

4. The polysiloxanes according to claim 1 wherein elements of formula VIII are absent or substantially absent.

5. The polysiloxanes according to claim 1 wherein $R^1$ is derived from a benzalmalonate and $R^2$ is derived from an amino substituted hydroxybenzophenone.

6. A light screening agent which comprises at least one polysiloxane according to claim 1.

7. The light screening agent according to claim 6 for the protection of human skin and/or human hair.

8. The light screening agent according to claim 6 for the protection of UV sensitive plastic materials and medicinal products.

9. Cosmetic or pharmaceutical compositions comprising at least one polysiloxane as defined in claim 1 and at least one pharmaceutically and/or cosmetically acceptable excipient.

10. The cosmetic or pharmaceutical compositions according to claim 9 which additionally further comprises at least one UV-A screening agent, UV-B screening agent and broadband screening agent.

11. The cosmetic or pharmaceutical compositions according to claim 9 comprising from 0.2 wt. %-20 wt. % the polysiloxanes based on the total weight of the composition.

12. The cosmetic or pharmaceutical compositions according to claim 9 for topical application onto human skin and/or hair.

13. The polysiloxanes according to claim 1, wherein the number of elements of at least one of the groups (A), (B), (C) and (D) is 5 to 60.

14. The polysiloxanes according to claim 1, wherein the number of elements of formula (VII) is 5 to 80.

15. The cosmetic or pharmaceutical compositions according to claim 9 comprising from 0.5 wt. % to 12 wt. % of the polysiloxanes based on the total weight of the composition.

* * * * *